United States Patent
Ohno et al.

(10) Patent No.: US 7,064,240 B2
(45) Date of Patent: Jun. 20, 2006

(54) PROCESS FOR PRODUCING PERFLUOROCARBONS AND USE THEREOF

(75) Inventors: Hiromoto Ohno, Kawasaki (JP); Toshio Ohi, Kawasaki (JP)

(73) Assignee: Showa Denko K.K., Tokyo (JP)

(*) Notice: Subject to any disclaimer, the term of this patent is extended or adjusted under 35 U.S.C. 154(b) by 241 days.

(21) Appl. No.: 10/258,172

(22) PCT Filed: Feb. 21, 2002

(86) PCT No.: PCT/JP02/01549
§ 371 (c)(1),
(2), (4) Date: Oct. 22, 2002

(87) PCT Pub. No.: WO02/066408
PCT Pub. Date: Aug. 29, 2002

(65) Prior Publication Data
US 2003/0163008 A1    Aug. 28, 2003

Related U.S. Application Data
(60) Provisional application No. 60/272,451, filed on Mar. 2, 2001.

(30) Foreign Application Priority Data
Feb. 23, 2001  (JP) .......................................... 2001-48985

(51) Int. Cl.
C07C 17/00  (2006.01)
C07C 19/08  (2006.01)
C07C 21/18  (2006.01)
C07C 17/08  (2006.01)

(52) U.S. Cl. ........................ 570/161; 570/164; 570/165; 570/166; 570/167; 570/168; 570/169

(58) Field of Classification Search ................. 570/161, 570/164, 165, 166, 167, 168, 169
See application file for complete search history.

(56) References Cited

U.S. PATENT DOCUMENTS

| 4,158,023 A | * | 6/1979 | von Halasz | ................. 570/166 |
| 4,377,715 A | * | 3/1983 | Nychka et al. | ............. 570/123 |
| 6,136,214 A |   | 10/2000 | Mori et al. | |

FOREIGN PATENT DOCUMENTS

| CN | 1161952 A | 10/1997 |
| GB | 2 311 522 A | 10/1997 |
| JP | 9-241186 A | 9/1997 |
| WO | WO 96/09271 A1 | 3/1996 |

* cited by examiner

Primary Examiner—Elvis O. Price
(74) Attorney, Agent, or Firm—Sughrue Mion, PLLC

(57) ABSTRACT

The process for producing perfluorocarbons according to the present invention is characterized in that in the production of a perfluorocarbon by contacting an organic compound with a fluorine gas, the organic compound is contacted with the fluorine gas at a temperature of from 200 to 500° C. and the content of an oxygen gas within the reaction system is controlled to 2% by volume or less based on the gas components in the reaction starting material, whereby a perfluorocarbon reduced in the content of impurities is produced. According to the process for producing perfluorocarbons of the present invention, high-purity perfluorocarbons extremely suppressed in the production of impurities such as oxygen-containing compound can be obtained. The perfluorocarbons obtained by the production process of the present invention contain substantially no oxygen-containing compound and therefore, can be effectively used as an etching or cleaning gas for use in the process for producing a semiconductor device.

16 Claims, No Drawings

PROCESS FOR PRODUCING PERFLUOROCARBONS AND USE THEREOF

CROSS REFERENCES OF RELATED APPLICATION

This application is a 371 of PCT/JP02/01549, filed Feb. 21, 2002, which claims benefit to Provisional application 60/272,451 filed Mar. 2, 2001 pursuant to 35 U.S.C. §111(b).

TECHNICAL FIELD

The present invention relates to a process for producing perfluorocarbons, more specifically, the present invention relates to a process for producing perfluorocarbons useful for the production of semiconductor devices and reduced in the production of impurities such as oxygen-containing compound.

The present invention also relates to high-purity perfluorocarbons containing substantially no oxygen-containing compound, a perfluorocarbon-containing gas, and uses thereof.

BACKGROUND ART

In the production process of semiconductor devices, perfluorocarbons have been conventionally used as one of useful etching or cleaning gases.

On the other hand, to keep up with recent tendency toward higher performance, smaller size, higher density wiring and the like of electrical or electronic equipment, the electrode of a circuit substrate is becoming finer and in order to form a circuit pattern with higher precision by etching or the like, use of an extremely high-purity etching gas from which impurities are eliminated as much as possible is demanded. When the etching gas contains an impurity even if in a very small amount, this may cause generation of a large width line in the formation of a fine pattern or increase of defects in the product having a high density integrated circuit.

Also, the process of removing deposits using a cleaning gas must be performed to let residual impurities be reduced as much as possible in the production process of a semiconductor device after the cleaning so as to provide a high-purity and high-quality device. For this purpose, a high-purity cleaning gas containing substantially no impurity is demanded.

With respect to the process for producing perfluorocarbons, various methods have been heretofore proposed. For example, as for tetrafluoromethane, a method of reacting chlorotrifluoromethane with HF in the presence of a catalyst (see, JP-B-62-10211 (the term "JP-B" as used herein means an "examined Japanese patent publication")) and a method of reacting dichlorodifluoromethane with HF in the presence of a catalyst (see, JP-B-42-3004) are known; and as for hexafluoroethane, an electrolytic fluorination method starting from ethane and/or ethylene, a pyrolysis method of thermally decomposing tetrafluoroethylene, and a method of fluorinating acetylene, ethylene, ethane or the like using a metal fluoride are known. Furthermore, a direct fluorination method of contacting hydrocarbon or hydrofluorocarbon with a fluorine gas is also known and examples thereof include a method of reacting trifluoromethane with a fluorine gas (see, GB 1,116,920), a method of reacting tetrafluoroethane with a fluorine gas (see, Japanese Patent 2,947,158), a method of reacting hexafluoropropylene with a fluorine gas (see, JP-B-62-61572), and a method of reacting carbon (C) with $F_2$ in $BrF_3$ or $IF_3$ (see, JP-A-58-162536). Other than these, in the case of octafluoropropane as a perfluorocarbon having 3 carbon atoms, a direct fluorination method of reacting propane with a fluorine gas is known (see, EP 31519).

Of these various production processes, the direct fluorination method uses a fluorine gas having an extremely high reactivity and therefore, incurs dangers of bringing about explosion, corrosion or the like between the substrate organic compound and the fluorine gas and furthermore, dangers of causing side reactions such as abrupt reaction or explosion resulting from cleavage of C—C bond, polymerization, production of carbon (C), volume or the like due to generation of heat.

For example, in the case of synthesizing a perfluorocarbon by the direct fluorination method of reacting a linear hydrocarbon compound with a fluorine gas, the synthesis is accompanied with a very large heat of reaction as shown below.

$$CH_4 + 4F_2 \rightarrow CF_4 + 4HF \quad \text{(Equation 1)}$$

($\Delta H = -479$ kcal/mol)

$$C_2H_6 + 6F_2 \rightarrow C_2F_6 + 6HF \quad \text{(Equation 2)}$$

($\Delta H = -690$ kcal/mol)

As such, in replacing one C—H bond by C—F bond, a heat of reaction of about −110 Kcal/mol is generated. In the direct fluorination method of reacting propane ($C_3H_8$) with a fluorine gas, $\Delta H$ is about −880 Kcal/mol.

In the case of starting from methane (Equation 1), 4 mol of fluorine gas is necessary per 1 mol of methane and in the case of starting from ethane (Equation 2), 6 mol of fluorine gas is necessary per 1 mol of ethane. In this way, as the number of hydrogen atoms in the substrate organic compound is larger or as the amount of fluorine used is larger, the heat of reaction becomes larger. In order to prevent the abrupt generation of heat of reaction in the direct fluorination method, there have been proposed, for example, a method of diluting the fluorine gas with another inert gas (e.g., nitrogen, helium), a method of diluting a substrate organic compound with another inert gas, a method of dissolving a substrate organic compound in a solvent inactive to fluorine in a low concentration, a method of performing the reaction in a low temperature region or a method of designing an apparatus such as jet reactor to allow the fluorine gas to gradually come into contact with the substrate organic compound when the reaction is performed in a gas phase.

The present inventors have already found that these problems encountered in the direct fluorination method can be solved by appropriately controlling the reaction conditions in the direct fluorination method and thereby, perfluorocarbons can be safely and economically produced in industry with good efficiency (Japanese Patent 3,067,633).

In the case of using the thus-obtained perfluorocarbons as a cleaning or etching gas in the process for producing a semiconductor device or the like, the perfluorocarbon must be free of various impurities as much as possible and have a high purity as described above. For the removal of impurities, separation by distillation or the like is usually used. Heretofore, perfluorocarbons having a fixed purity have been produced by the direct fluorination method where impurities are removed to a certain purity by combining, for example, purification of starting materials, and distillation and purification of the product.

In the process of studying the above-described method for obtaining perfluorocarbons by the direct fluorination method, the present inventors have found that some components remain as impurities even by performing high-precision distillation or the like and these residual impurities cannot be easily and effectively removed. By the analysis of these impurities, oxygen-containing compounds such as perfluorodimethyl ether, perfluorodimethyl peroxide and perfluoromethyl ethyl ether were detected. These oxygen-containing compounds were very difficult to remove because these formed an azeotropic composition or azeotrope-like mixture with perfluorocarbons. If such a perfluorocarbon is used as an etching or cleaning gas for the manufacture of a semiconductor device while allowing mixing of those oxygen-containing compounds in a high concentration, the requirement for formation of a very fine pattern may not be satisfied.

Accordingly, the present inventors have made extensive investigations to prevent the production of such oxygen-containing compounds, as a result, it has been found that these oxygen-containing compounds are originated in the oxygen gas contained in a slight amount in the reaction starting materials such as fluorine gas or hydrofluorocarbon, and when the oxygen gas content in the reaction starting materials is reduced to a specific amount or less while controlling the reaction conditions such as reaction temperature to fall within a certain range, the production of those oxygen-containing compounds can be effectively prevented. The present invention has been accomplished based on this finding. To the best knowledge of the present inventors, there has been not found a process for producing perfluorocarbons, which involves a technique of preventing the production of oxygen-containing compounds originated in the oxygen gas in starting materials.

OBJECT OF THE INVENTION

The present invention has been made to overcome the above-described problems in conventional techniques and the object of the present invention is to provide high-purity perfluorocarbons suppressed from the production of impurities such as oxygen-containing compound, and provide a production process therefor. The object of the present invention includes providing uses of the high-purity perfluorocarbons.

SUMMARY OF THE INVENTION

The process for producing perfluorocarbons according to the present invention is characterized in that in the production of perfluorocarbons from a reaction starting material comprising an organic compound and a fluorine gas, the organic compound is contacted with the fluorine gas at a temperature of from 200 to 500° C. while controlling the content of an oxygen gas within the reaction system to 2% by volume or less based on the gas components in the reaction starting material to produce a perfluorocarbon reduced in the content of impurities.

The organic compound and the fluorine gas are preferably contacted in the presence of a diluting gas.

The organic compound is preferably an aliphatic saturated compound having 6 or less carbon atoms and/or an aliphatic unsaturated compound having 6 or less carbon atoms.

The organic compound is more preferably an aliphatic saturated compound having 6 or less carbon atoms, still more preferably a hydrofluorocarbon, and particularly preferably at least one member selected from the group consisting of fluoromethane, difluoromethane, trifluoromethane, trifluoroethane, tetrafluoroethane, pentafluoroethane, pentafluoropropane, hexafluoropropane and heptafluoropropane.

In the process for producing perfluorocarbons, which is a process for producing a perfluorocarbon by contacting the organic compound with the fluorine gas in a gas phase using no catalyst in the presence of a diluting gas, the oxygen gas contained in the fluorine gas before the contact between the organic compound and the fluorine gas is preferably in an amount of 1% by volume or less based on said fluorine gas. In this case, the organic compound is preferably a hydrofluorocarbon having 4 or less carbon atoms, more preferably at least one member selected from the group consisting of difluoromethane, trifluoromethane, trifluoroethane, tetrafluoroethane, pentafluoroethane, hexafluoropropane and heptafluoropropane.

The amount of fluorine gas introduced into the reaction system is preferably 9% by volume or less based on the total amount of gas components within the reaction system.

The diluting gas is at least one member selected from the group consisting of tetrafluoromethane, hexafluoroethane, octafluoropropane and hydrogen fluoride.

The diluting gas preferably contains hydrogen fluoride and the content of the hydrogen fluoride is preferably 50% by volume or more based on the entire amount of diluting gas.

The impurity may be an oxygen-containing compound.

The process for producing perfluorocarbons may further comprise a step of adsorbing and thereby removing the oxygen-containing compound.

The oxygen-containing compound can be adsorbed and thereby removed by activated carbon.

The perfluorocarbon is preferably at least one member selected from the group consisting of tetrafluoromethane, hexafluoroethane and octafluoropropane.

The total amount of oxygen-containing compounds contained in the perfluorocarbons is preferably 5 ppm by volume or less, more preferably 2 ppm by volume or less.

The perfluorocarbon-containing gas of the present invention contains the above-described perfluorocarbons.

The etching gas of the present invention is characterized by comprising the above-described perfluorocarbon-containing gas, and the perfluorocarbon is preferably tetrafluoromethane.

The cleaning gas of the present invention is characterized by comprising the above-described perfluorocarbon-containing gas, and the perfluorocarbon is preferably hexafluoroethane or octafluoropropane.

DETAILED DESCRIPTION OF THE INVENTION

The process for producing perfluorocarbons according to the present invention and uses thereof are described in detail below.

[Process for Producing Perfluorocarbons]

The process for producing perfluorocarbons according to the present invention is a process for producing a perfluorocarbon by contacting an organic compound with a fluorine gas ($F_2$), where the content of oxygen gas contained in the reaction system is controlled to a fixed amount or less. The process for producing perfluorocarbons according to the present invention may be performed, if desired, in the presence of a diluting gas.

(Organic Compound)

The organic compound which can be used in the present invention is not particularly limited and known organic compounds used in the production of perfluorocarbon may be used.

Examples of the organic compound include aliphatic saturated compounds having 6 or less carbon atoms and aliphatic unsaturated compounds having 6 or less carbon atoms. At least one organic compound selected from these compounds is preferably used. Among these compounds, the organic compound for use in the present invention is more preferably at least one aliphatic saturated compound having 6 or less carbon atoms.

Examples of the aliphatic saturated compound having 6 or less carbon atoms include hydrofluorocarbons such as fluoromethane, difluoromethane, tifluoromethane, trifluoroethane, tetrafluoroethane, pentafluoroethane, pentafluoropropane, hexafluoropropane and heptafluoropropane. The aliphatic saturated compound is preferably at least one hydrofluorocarbon selected from these compounds.

In the case where the organic compound and the fluorine gas are contacted in a gas phase using no catalyst in the presence of a diluting gas, the organic compound is preferably a hydrofluorocarbon having 4 or less carbon atoms.

Examples of this hydrofluorocarbon include difluoromethane, trifluoromethane, tetrafluoroethane, pentafluoroethane, hexafluoropropane and heptafluoropropane. The organic compound is preferably at least one hydrofluorocarbon selected from these compounds.

Perfluorocarbons such as tetrafluoromethane, hexafluoroethane and octafluoropropane can be preferably obtained starting from the above-described hydrofluorocarbons.

(Fluorine Gas)

The fluorine gas for use in the present invention can be produced by a known method such as electrolysis of hydrogen fluoride. Also, a commercially available fluorine gas can be used.

(Diluting Gas)

Examples of the diluting gas which can be used in the present invention include tetrafluoromethane, hexafluoroethane, octafluoropropane and hydrogen fluoride.

These diluting gases may be used individually or in combination of two or more thereof. Among these diluting gases, hydrogen fluoride is preferred. In the case of using hydrogen fluoride with another diluting gas, the gas used in combination is preferably a gas rich in hydrogen fluoride. More specifically, hydrogen fluoride is preferably in an amount of 50% by volume or more, more preferably 60% by volume or more, based on the entire diluting gas.

Process for Producing Perfluorocarbons

In the case where tetrafluoroethane ($CF_3CH_2F$) or trifluoromethane ($CHF_3$) is used as the starting material organic compound and contacted with a fluorine gas to produce tetrafluoromehtane ($CF_4$) or hexafluoroethane ($CF_3CF_3$), if an oxygen gas is present in the starting materials (organic compound and fluorine gas), oxygen-containing compounds such as $CF_3OCF_3$, $CF_3OOCF_3$ and $CF_3CF_2OCF_3$ are produced. These oxygen-containing compounds form an azeotropic composition or azeotrope-like mixture with the objective product and it is very difficult to separate these oxygen-containing compounds from the objective product by a known method such as distillation.

In the process for producing perfluorocarbons according to the present invention, the organic compound and the fluorine gas ($F_2$) are contacted to produce a perfluorocarbon and at this time, the content of an oxygen gas contained in the reaction gas is suitably controlled to 2% by volume or less, preferably 1% by volume or less, more preferably 0.5% by volume or less, based on the gas components within the reaction system.

The term "reaction system" as used herein means a reaction solution or gas phase atmosphere containing a reaction starting material comprising an organic compound and a fluorine gas, and if desired, further containing a diluting gas, within a reactor where the organic compound and the fluorine gas are actually contacted. The reaction system is the above-described reaction solution or gas phase atmosphere within a reactor between the charging of starting materials and the completion of reaction but excludes the reaction solution or gas phase atmosphere in the steps after the completion of reaction, such as extraction and purification.

The reaction between the organic compound and the fluorine gas may also be performed in a gas phase using no catalyst in the presence of a diluting gas. In this case, the content of an oxygen gas containing in the starting material fluorine gas is preferably controlled to 1% by volume or less, more preferably 0.6% by volume or less, still more preferably 0.4% by volume or less, based on the fluorine gas.

When the oxygen gas content in the reaction system is less than 2% by volume, high-purity perfluorocarbons substantially free of the above-described oxygen-containing compounds can be produced. Furthermore, when the oxygen gas content in the fluorine gas is reduced to 1% by volume or less, more high-purity perfluorocarbons substantially free of oxygen-containing compounds can be produced.

If the amount of oxygen gas contained within the reaction system exceeds 2% by volume, a significant amount of oxygen-containing compounds are produced.

In order to control the oxygen gas content within the reaction system and in the fluorine gas to fall within the above-described range, it is necessary to perform the reaction in a closed system not to allow an oxygen gas from mingling into the reactor from the outside and to remove an oxygen gas from the reaction starting materials such as organic compound, fluorine gas and diluting gas. In the case where a part of the gas after the reaction is circulated and used as a diluting gas, the possibility of an oxygen gas mingling from the outside advantageously decreases. The oxygen gas contained in the organic compound, fluorine gas and diluting gas can be removed by a known method. This may be attained by separating impurities in the starting materials, for example, through distillation of reaction starting materials or adsorption using an adsorbent such as activated carbon.

In the case of contacting the organic compound with the fluorine gas in the presence of a diluting gas, either one or both of the reaction substrate (organic compound) and the fluorine gas may be diluted with a diluting gas before charging the organic compound or fluorine gas into the reactor.

Of these, the fluorine gas is preferably diluted with a diluting gas before charging.

In this case, the amount of fluorine gas introduced into the reaction system is preferably 9% by volume or less, more preferably 8% by volume or less, based on the total amount of gas components within the reaction system. In the case of continuously performing the reaction, the amount of fluorine gas introduced into the reaction system is preferably controlled to always fall within the above-described range. Incidentally, the gas components within the reaction system means fluorine gas, organic compound and diluting gas within the reaction system.

As described above, the direct fluorination method of producing a perfluorocarbon using a fluorine gas uses a fluorine gas extremely rich in reactivity and therefore, when the substrate organic compound, particularly hydrogen-containing compound, in a high concentration is exposed to fluorine, this may incur combustion or explosion. When the fluorine gas concentration is 9% by volume or less at the inlet of the reactor, the mixed gas concentration can be outside the range of explosion and the reaction between the fluorine gas and the organic compound can be performed safely in industry.

In the present invention, the reaction temperature on contacting the organic compound with the fluorine gas is suitably from 200 to 500° C., preferably from 300 to 450° C.

When the reaction temperature is within this range, the production of oxygen-containing compounds produced as impurities originated in the oxygen gas can be remarkably reduced. If the reaction temperature exceeds 500° C., even if the oxygen gas (concentration) within the reaction system is controlled to 2% by volume or less or the oxygen gas concentration in the fluorine gas is controlled to 1% by volume or less, a significant amount of oxygen-containing compounds are sometimes produced. Accordingly, in the present invention, the reaction temperature preferably controlled within the above-described range. This control of the reaction temperature is preferably performed without fail using, for example, thermocouple such that the reaction temperature does not exceed 500° C. not only in the reaction zone within the reactor but also in the portions where the organic compound or the fluorine gas is present.

According to the present invention, the mingling of oxygen-containing compounds is outstandingly prevented, however, in the case where the obtained crude perfluorocarbon contains a slight amount of oxygen containing compounds or impurities such as nitrogen, carbon monoxide and carbon dioxide, a step of adsorbing and thereby removing these compounds or impurities using activated carbon or the like is preferably provided.

The activated carbon used here may be a known activated carbon and among known activated carbons, coconut shell carbon can be preferably used. The separating and thereby removing operation may be performed in either liquid phase or gas phase but is preferably performed in gas phase.

Perfluorocarbons

The total amount of oxygen-containing compounds contained in the thus-obtained perfluorocarbons can be reduced to, in the case of crude perfluorocarbons before purification, preferably 5 ppm by volume or less, more preferably 2 ppm by volume or less, still more preferably 1 ppm by volume or less. Thus, according to the production process of the present invention, high-purity perfluorocarbons remarkably reduced in the content of oxygen-containing compounds can be obtained without passing through a purification step such as distillation or adsorption.

Also, by passing the purification step, the total content of oxygen-containing compounds can be reduced to preferably 1 ppm by volume or less, more preferably 0.5 ppm by volume or less, still more preferably 0.4 ppm by volume or less. Thus, according to the production process of the present invention, high-purity perfluorocarbons more reduced in the content of oxygen-containing compounds can be very easily and simply obtained.

The oxygen-containing compounds can be detected (analyzed) using analysis methods such as TCD, FID and DID methods of gas chromatography (GC), and gas chromatography-mass spectrometer (GC-MS).

[Perfluorocarbons-Containing Gas and Use Thereof]

The perfluorocarbons obtained by the production process of the present invention are satisfactorily reduced in impurities such as oxygen-containing compound and therefore, can be used over a wide range. For example, the compound which is a gas at ordinary temperature can be used as an etching gas at the etching step in the production process of a semiconductor device and the compound which is a liquid at ordinary temperature can be used as a cooling solvent or the like.

More specifically, in the production process of a semiconductor device such as LSI and TFT, the compound can be suitably used as an etching gas for forming a circuit pattern after forming a thin or thick film using a CVD method, a sputtering method or a vapor deposition method.

The compound can also be used as a cleaning gas at the cleaning step in the production process of a semiconductor device.

In the case of using the perfluorocarbons of the present invention as an etching gas, tetrafluoromethane is preferred and in the case of using as a cleaning gas, hexafluoroethane or octafluoropropane is preferred.

More specifically, in an apparatus for forming a thin or thick film, cleaning is performed to remove unnecessary deposits accumulated on the inner wall of the apparatus, a jig and the like, because unnecessary deposits produced cause generation of particles and must be removed on occasions for producing a film of good quality. The perfluorocarbons according to the present invention can be suitably used as a cleaning gas therefor.

The gas containing a high-purity perfluorocarbon according to the present invention is a gas containing a perfluorocarbon which is a gas at ordinary temperature. The gas may contain the perfluorocarbon alone or may appropriately contain other gas. Examples of the other gas include inert gases such as He, Ne and Ar. The amount of the other gas blended is not particularly limited. For example, in the case of using the high-purity perfluorocarbons according to the present invention as an etching or cleaning gas, the amount of the other gas blended varies depending on the kind, thickness and the like of the compound to be etched and can be determined according to the amount and thickness of the deposit to be cleaned.

Effect of the Invention

According to the process for producing perfluorocarbons of the present invention, the oxygen gas content in the reaction system is reduced to a specific amount or less, so that high-purity perfluorocarbons extremely suppressed in the production of impurities such as oxygen-containing compound can be obtained. The perfluorocarbons obtained by the production process of the present invention contain substantially no oxygen-containing compound and therefore, can be effectively used as an etching or cleaning gas for use in the process for producing a semiconductor device.

EXAMPLES

The present invention is described in greater detail below by referring to Examples, however, the present invention should not be construed as being limited to these Examples.

Preparation Example 1

A fluorination reaction was performed by contacting chloroform ($CHCl_3$) and hydrogen fluoride (HF) in gas phase in the presence of a fluorination catalyst. The reaction product was purified by a known distillation method to obtain crude trifluoromethane ($CHF_3$). The obtained crude trifluoromethane was analyzed by gas chromatography and found to have the following composition.

| | |
|---|---|
| CHF$_3$ | 97.2667 |
| Other organic impurities | 0.1126 |
| Oxygen gas | 1.2081 |
| Nitrogen gas | 1.4126 |
| | unit: % by volume |

Incidentally, other impurities such as CHClF$_2$ and CClF$_3$ were contained.

The results obtained are shown in Table 1.

Preparation Example 2

A distillation operation was repeatedly applied to the crude trifluoromethane obtained in Preparation Example 1. The obtained trifluoromethane was analyzed by gas chromatography and found to have the following composition.

| | |
|---|---|
| CHF$_3$ | 99.8288 |
| Other organic impurities | 0.0208 |
| Oxygen gas | 0.0720 |
| Nitrogen gas | 0.0784 |
| | unit: % by volume |

The results obtained are shown in Table 1.

Preparation Example 3

A fluorination reaction was performed by contacting trichloroethylene and hydrogen fluoride in gas phase in the presence of a fluorination catalyst. The reaction product was purified by a known distillation method to obtain crude tetrafluoroethane (CF$_3$CH$_2$F). The obtained crude tetrafluoroethane was analyzed by gas chromatography and found to have the following composition.

| | |
|---|---|
| CF$_3$CH$_2$F | 97.0359 |
| Other organic impurities | 0.5124 |
| Oxygen gas | 1.3314 |
| Nitrogen gas | 1.1203 |
| | unit: % by volume |

Incidentally, other impurities such as CF$_3$CH$_3$, CF$_3$CHF$_2$ and CHF$_2$CHF$_2$ were contained.

The results obtained are shown in Table 1.

Preparation Example 4

A distillation operation was repeatedly applied to the crude tetrafluoroethane obtained in Preparation Example 3. The obtained tetrafluoroethane was analyzed by gas chromatography and found to have the following composition.

| | |
|---|---|
| CF$_3$CH$_2$F | 99.9018 |
| Other organic impurities | 0.0088 |
| Oxygen gas | 0.0402 |
| Nitrogen gas | 0.0492 |
| | unit: % by volume |

The results obtained are shown in Table 1.

Preparation Example 5

A fluorine gas was obtained by the electrolysis of hydrogen fluoride. The obtained fluorine gas was sampled using an SUS cylinder (having an inner surface subjected to a passivation treatment) and after removing fluorine, analyzed by gas chromatography. As a result, the oxygen gas in the fluorine gas was found to have the following concentration value.

| | | |
|---|---|---|
| Oxygen gas | 1.3825 | unit: % by volume |

The main component in the remaining was fluorine and nitrogen gas, hydrogen fluoride and the like were contained.

Preparation Example 6

The starting material obtained in Preparation Example 5 was further subjected to a purification operation (e.g., cooling) and analyzed in the same manner as in Preparation Example 5. As a result, the oxygen gas in the fluorine gas was found to have the following concentration value.

| | | |
|---|---|---|
| Oxygen gas | 0.3020 | unit: % by volume |

The results obtained are shown in Table 1.

Example 1

An Inconel 600-made reactor having an inner diameter of 20.6 mmØ and a length of 500 mm (electric heater heating system, the reactor was subjected to a passivation treatment with a fluorine gas at a temperature of 600° C.) was heated to a temperature of 420° C. while feeding a nitrogen gas at 30 NL/hr. Thereafter, hydrogen fluoride was fed at 50 NL/hr and furthermore, while passing a diluting gas comprising those nitrogen and hydrogen fluoride was into one side of branched gas flow, the trifluoromethane obtained in Preparation Example 2 was flowed at 3.6 NL/hr.

Thereafter, while passing the same diluting gas comprising nitrogen and hydrogen fluoride into another side of branched gas flow, the fluorine gas prepared in Preparation Example 6 was fed at a flow rate of 3.9 NL/hr, thereby performing the reaction.

After 3 hours, the reaction outlet gas was treated with an aqueous potassium hydroxide solution and an aqueous potassium iodide solution to remove hydrogen fluoride and unreacted fluorine gas and then analyzed by gas chromatography. The analysis results of the organic composition except for oxygen and nitrogen portions are shown below.

| | |
|---|---|
| CF$_4$ | 98.7992 |
| CF$_3$CF$_3$ | 0.4808 |
| Others | 0.7200 |
| | unit: % by volume |

"Others" were C$_3$F$_8$, CClF$_3$ and the like and the total amount of CF$_3$OCF$_3$ and CF$_3$OOCF$_3$ as oxygen-containing compounds was 2 ppm by volume or less.

Thereafter, the reaction outlet gas was treated with an aqueous potassium hydroxide solution and an aqueous potassium iodide solution to remove hydrogen fluoride and unreacted fluorine gas and the resulting gas was passed through a dehydrating agent, collected in an SUS cylinder under cooling, and then distillation-purified by a known distillation operation to obtain tetrafluoromehtane. The organic composition thereof was analyzed by gas chromatography and gas chromatography-mass spectrometer. The results are shown below.

| | |
|---|---|
| $CF_3OCF_3$ | <0.2 ppm by volume |
| $CF_3OOCF_3$ | <0.2 ppm by volume |
| Others | <2.0 ppm by volume |
| $CF_4$ | >99.9997% by volume |

The total amount of oxygen-containing compounds was 0.5 ppm by volume or less.

The results obtained are shown in Table 2.

Example 2

While feeding a nitrogen gas at 30 NL/hr, the same reactor as in Example 1 was heated to a temperature of 370° C. Then, hydrogen fluoride was fed at 50 NL/hr and furthermore, while passing a diluting gas comprising those nitrogen and hydrogen fluoride into one side of branched gas flow, a gas mainly comprising the tetrafluoroethane prepared in Preparation Example 4 was flowed at 1.8 NL/hr. Thereafter, while passing the same diluting gas into another side of branched gas flow, the fluorine gas prepared in Preparation Example 6 was fed at 3.9 NL/hr, thereby performing the reaction.

After 3 hours, the reaction outlet gas was treated with an aqueous potassium hydroxide solution and an aqueous potassium iodide solution to remove hydrogen fluoride and unreacted fluorine gas and then analyzed by gas chromatography. The analysis results of the organic composition except for oxygen and nitrogen portions are shown below.

| | |
|---|---|
| $CF_3CF_3$ | 98.4875 |
| $CF_3CHF_2$ | 0.0025 |
| $CF_4$ | 0.7280 |
| Others | 0.7820 |
| | unit: % by volume |

"Others" were mainly $C_3F_8$ and the total amount of $CF_3CF_2OCF_3$, $CF_3OCF_3$ and $CF_3OOCF_3$ as oxygen-containing compounds was 1 ppm by volume or less.

Thereafter, the reaction outlet gas was treated with an aqueous potassium hydroxide solution and an aqueous potassium iodide solution to remove hydrogen fluoride and unreacted fluorine gas and the resulting gas was passed through a dehydrating agent, collected in an SUS cylinder under cooling, and then distillation-purified by a known distillation operation to obtain hexafluoroethane ($CF_3CF_3$). The organic composition thereof was analyzed by gas chromatography and gas chromatography-mass spectrometer. The results are shown below.

| | |
|---|---|
| $CF_3OCF_3$ | <0.2 ppm by volume |
| $CF_3OOCF_3$ | <0.1 ppm by volume |
| $CF_3CF_2OCF_3$ | <0.1 ppm by volume |
| Others | <2.0 ppm by volume |
| $CF_3CF_3$ | >99.9997% by volume |

The results obtained are shown in Table 2.

Comparative Example 1

While feeding a nitrogen gas at 30 NL/hr, the same reactor as in Example 1 was heated to a temperature of 450° C. Then, hydrogen fluoride was fed at 50 NL/hr and furthermore, while passing a diluting gas comprising those nitrogen and hydrogen fluoride into one side of branched gas flow, a gas mainly comprising the tetrafluoromethane prepared in Preparation Example 1 was flowed at 3.6 NL/hr. Thereafter, while passing the same diluting gas into another side of branched gas flow, the fluorine gas prepared in Preparation Example 5 was fed at 3.9 NL/hr, thereby performing the reaction.

After 3 hours, the reaction outlet gas was treated with an aqueous potassium hydroxide solution and an aqueous potassium iodide solution to remove hydrogen fluoride and unreacted fluorine gas and then analyzed by gas chromatography. The analysis results of the organic composition except for oxygen and nitrogen are shown below.

| | |
|---|---|
| $CF_4$ | 98.3618 |
| $CF_3CF_3$ | 0.4988 |
| Others | 1.1123 |
| $CF_3OCF_3$ | 0.0146 (146 ppm) |
| $CF_3OOCF_3$ | 0.0125 (125 ppm) |
| | unit: % by volume |

With a total oxygen content (concentration) of 2% or more in the starting material, a significant amount of oxygen-containing compounds as impurities were produced.

The results obtained are shown in Table 2.

Comparative Example 2

While feeding a nitrogen gas at 30 NL/hr, the same reactor as in Example 1 was heated to a temperature of 430° C. Then, hydrogen fluoride was fed at 50 NL/hr and furthermore, while passing a diluting gas comprising those nitrogen and hydrogen fluoride into one side of branched gas flow, a gas mainly comprising the tetrafluoroethane prepared in Preparation Example 3 was flowed at 1.8 NL/hr. Thereafter, while passing the same diluting gas into another side of branched gas flow, the fluorine gas prepared in Preparation Example 5 was fed at 3.9 NL/hr, thereby performing the reaction.

After 3 hours, the reaction outlet gas was treated with an aqueous potassium hydroxide solution and an aqueous potassium iodide solution to remove hydrogen fluoride and unreacted fluorine gas and then analyzed by gas chromatography. The analysis results of the organic composition except for oxygen and nitrogen are shown below.

| | |
|---|---|
| $CF_3CF_3$ | 97.1841 |
| $CF_4$ | 0.8920 |
| Others | 1.8920 |
| $CF_3OCF_3$ | 0.0133 (133 ppm) |
| $CF_3OOCF_3$ | 0.0088 (88 ppm) |
| $CF_3CF_2OCF_3$ | 0.0098 (98 ppm) |
| | unit: % by volume |

Thereafter, the reaction outlet gas was treated with an aqueous potassium hydroxide solution and an aqueous potassium iodide solution to remove hydrogen fluoride and unreacted fluorine gas and the resulting gas was passed through a dehydrating agent, collected in an SUS cylinder under cooling, and then distillation-purified by a known distillation operation to obtain hexafluoroethane. The organic composition thereof was analyzed by gas chromatography and gas chromatography-mass spectrometer. The results are shown below.

| | |
|---|---|
| $CF_3CF_3$ | >99.9866% by volume |
| $CF_4$ | <0.4 ppm by volume |
| Others | <2.0 ppm by volume |
| $CF_3OCF_3$ | 128 ppm by volume |
| $CF_3OOCF_3$ | 1 ppm by volume |
| $CF_3CF_2OCF_3$ | 1 ppm by volume |

$CF_3OCF_3$ forms an azeotropic mixture with the objective hexafluoroethane and the separation thereof is apparently difficult.

The results obtained are shown in Table 2.

Comparative Example 3

A gas obtained using the same reactor as in Example 1 thoroughly in the same conditions by the same operations except for changing the reaction temperature to 520° C. was analyzed by gas chromatography. The analysis results of the organic composition except for oxygen and nitrogen are shown below.

| | |
|---|---|
| $CF_4$ | 95.3548 |
| $CF_3CF_3$ | 1.6872 |
| Others | 2.8945 |
| $CF_3OCF_3$ | 0.0367 |
| $CF_3OOCF_3$ | 0.0268 |
| | unit: % by volume |

The results obtained are shown in Table 2.

TABLE 1

| | Product | Oxygen Gas Content (vol %) |
|---|---|---|
| Preparation Example 1 | trifluoromethane | 1.2081 |
| Preparation Example 2 | trifluoromethane | 0.0720 |
| Preparation Example 3 | tetrafluoroethane | 1.3314 |
| Preparation Example 4 | tetrafluoroethane | 0.0402 |
| Preparation Example 5 | $F_2$ | 1.3825 |
| Preparation Example 6 | $F_2$ | 0.3020 |

TABLE 2

| | Reaction Starting Material | Reaction Temperature (° C.) | Total Concentration of Oxygen Gas in Reaction Starting Material (% by volume) | Concentration of Oxygen-Containing Compounds in Perfluorocarbons (ppm by volume) | Concentration of Oxygen-Containing Compounds after Purification (ppm by volume) |
|---|---|---|---|---|---|
| Example 1 | Preparation Example 2 Preparation Example 6 | 420 | 0.3740 | 2 or less | 0.5 or less |
| Example 2 | Preparation Example 4 Preparation Example 6 | 370 | 0.3422 | 1 or less | 0.4 or less |
| Comparative Example 1 | Preparation Example 1 Preparation Example 5 | 450 | 2.5906 | 271 | |
| Comparative Example 2 | Preparation Example 3 Preparation Example 5 | 430 | 2.7139 | 319 | 130 |
| Comparative Example 3 | Preparation Example 2 Preparation Example 6 | 520 | 0.3740 | 635 | |

What is claimed is:

1. A process for producing perfluorocarbons, comprising, in the production of a perfluorocarbon from a reaction starting material comprising an organic compound and a fluorine gas, contacting said organic compound with said fluorine gas at a temperature of from 200 to 500° C. while controlling the content of an oxygen gas within the reaction system to 2% by volume or less based on the gas components in said reaction starting material to produce a perfluorocarbon reduced in the content of impurities.

2. The process for producing perfluorocarbons as claimed in claim 1, wherein said organic compound and said fluorine gas are contacted in the presence of a diluting gas.

3. The process for producing perfluorocarbons as claimed in claim 1, wherein said organic compound is an aliphatic saturated compound having 6 or less carbon atoms and/or an aliphatic unsaturated compound having 6 or less carbon atoms.

4. The process for producing perfluorocarbons as claimed in claim 1, wherein said organic compound is an aliphatic saturated compound having 6 or less carbon atoms.

5. The process for producing perfluorocarbons as claimed in claim 4, wherein said organic compound is at least one member selected from the group consisting of fluoromethane, difluoromethane, trifluoromethane, trifluoroethane, tetrafluoroethane, pentafluoroethane, pentafluoropropane, hexafluoropropane and heptafluoropropane.

6. The process for producing perfluorocarbons as claimed in claim 1, which is a process for producing perfluorocarbons by contacting said organic compound with said fluorine gas in a gas phase using no catalyst in the presence of a diluting gas, wherein said oxygen gas contained in said fluorine gas before the contact between said organic compound and said fluorine gas is in an amount of 1% by volume or less based on said fluorine gas.

7. The process for producing perfluorocarbons as claimed in claim 6, wherein said organic compound is a hydrofluorocarbon having 4 or less carbon atoms.

8. The process for producing perfluorocarbons as claimed in claim 7, wherein said organic compound is at least one member selected from the group consisting of difluoromethane, trifluoromethane, trifluoroethane, tetrafluoroethane, pentafluoroethane, hexafluoropropane and heptafluoropropane.

9. The process for producing perfluorocarbons as claimed in claim 1, wherein the amount of fluorine gas introduced into the reaction system is 9% by volume or less based on the total amount of gas components within the reaction system.

10. The process for producing perfluorocarbons as claimed in claim 2, wherein said diluting gas is at least one member selected from the group consisting of tetrafluoromethane, hexafluoroethane, octafluoropropane and hydrogen fluoride.

11. The process for producing perfluorocarbons as claimed in claim 10, wherein said diluting gas contains hydrogen fluoride and the content of said hydrogen fluoride is 50% by volume or more based on the entire amount of diluting gas.

12. The process for producing perfluorocarbons as claimed in claim 1, wherein said impurity is an oxygen-containing compound.

13. The process for producing perfluorocarbons as claimed in claim 1, which further comprises a step of adsorbing and thereby removing said oxygen-containing compound.

14. The process for producing perfluorocarbons as claimed in claim 13, wherein said oxygen-containing compound is adsorbed and thereby removed by activated carbon.

15. The process for producing perfluorocarbons as claimed in claim 1, wherein said perfluorocarbon is at least one member selected from the group consisting of tetrafluoromethane, hexafluoroethane and octafluoropropane.

16. The process for producing perfluorocarbons as claimed in claim 1, wherein the total amount of oxygen-containing compounds contained in said perfluorocarbons is 5 ppm by volume or less.

* * * * *